United States Patent [19]

Gilmore et al.

[11] Patent Number: 5,410,061

[45] Date of Patent: Apr. 25, 1995

[54] PHARMACEUTICAL COMPOUNDS

[75] Inventors: Jeremy Gilmore, Frimley; John R. Harris, Guildford, both of England

[73] Assignee: Lilly Industries Limited, Basingstoke, England

[21] Appl. No.: 962,365

[22] Filed: Oct. 16, 1992

[30] Foreign Application Priority Data

Oct. 24, 1991 [GB] United Kingdom ............... 9122590

[51] Int. Cl.$^6$ ............... C07D 401/10; C07D 401/12; A61K 31/475
[52] U.S. Cl. ................................ 546/152; 546/176
[58] Field of Search ............. 546/174, 175, 176, 152; 514/311, 314

[56] References Cited

U.S. PATENT DOCUMENTS

| | | | |
|---|---|---|---|
| 5,089,495 | 2/1992 | Crawley | 514/253 |
| 5,126,365 | 6/1992 | Bird | 514/45 L |
| 5,217,978 | 6/1993 | Bird | 514/312 |
| 5,240,941 | 8/1993 | Bruneau | 514/312 |
| 5,254,581 | 10/1993 | Bruneau | 514/460 |
| 5,283,245 | 2/1994 | Crawley | 514/249 |
| 5,288,742 | 2/1994 | Edwards | 514/365 |

FOREIGN PATENT DOCUMENTS 469833 7/1991 European Pat. Off. .
WO9106537 5/1991 WIPO .

OTHER PUBLICATIONS

Snyder, D. W., "Leukotriene Receptor ..." *Annu. Rev. Pharmacol. Toxicol.* vol. 29, pp. 123–143, 1989.

*Primary Examiner*—C. Warren Ivy
*Assistant Examiner*—D. Margaret M. Mach
*Attorney, Agent, or Firm*—Roger S. Benjamin

[57] ABSTRACT

A compound having pharmaceutical activity, of the formula

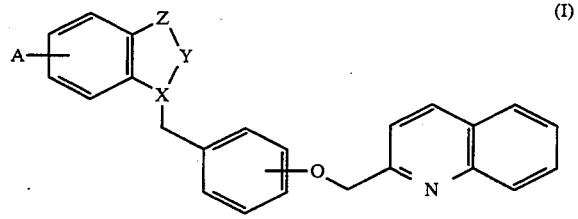

in which

A is hydrogen or $-(CR^1R^2)_xR^3$ where x is 0 or 1 to 4, $R^1$ and $R^2$ are each hydrogen or $C_{1-4}$ alkyl and $R^3$ is $-CN$, $-COOH$, tetrazolyl or $-CONHSO_2R^4$ where $R^4$ is optionally substituted phenyl, and $-X-Y-Z-$ is selected from

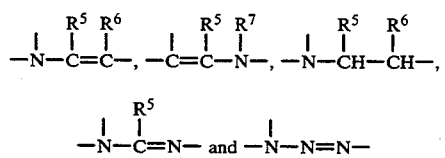

where $R^5$ and $R^6$ are each hydrogen, $C_{1-4}$ alkyl or $-(CR^1R^2)_xR^3$ where x, $R^1$, $R^2$ and $R^3$ are as defined above, and $R^7$ is hydrogen, $C_{1-4}$ alkyl or $-(CR^1R^2)_xR^3$ where x is 1 to 4, and $R^1$, $R^2$ and $R^3$ are as defined above;

provided that when A is hydrogen at least one of $R^5$, $R^6$ and $R^7$ is $-(CR^1R^2)_xR^3$, and provided that when

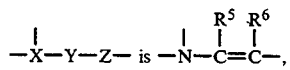

A is $-(CR^1R^2)_xR^3$ and x is 1 to 4 then $R^3$ is $-CONHSO_2R^4$;

and salts and esters thereof.

7 Claims, No Drawings

PHARMACEUTICAL COMPOUNDS

This invention relates to novel compounds, their preparation and pharmaceutical use.

The compounds of the invention are of the following formula

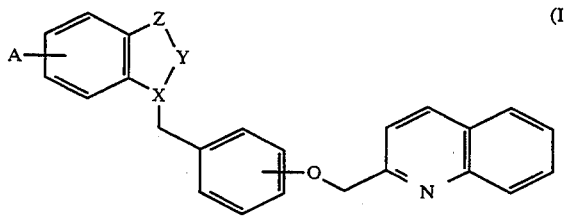
(I)

in which

A is hydrogen or —(CR$^1$R$^2$)$_x$R$^3$ where x is 0 or 1 to 4, R$^1$ and R$^2$ are each hydrogen or C$_{1-4}$ alkyl and R$^3$ is —CN, —COOH, tetrazolyl or —CONHSO$_2$R$^4$ where R$^4$ is optionally substituted phenyl, and

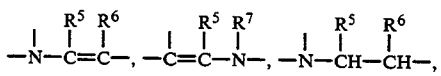 is selected from

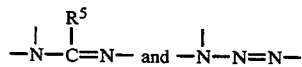

where R$^5$ and R$^6$ are each hydrogen, C$_{1-4}$ alkyl or —(CR$^1$R$^2$)$_x$R$^3$ where x, R$^1$, R$^2$ and R$^3$ are as defined above, and R$^7$ is hydrogen, C$_{1-4}$ alkyl or —(CR$^1$R$^2$)$_x$R$^3$ where x is 1 to 4, and R$^1$, R$^2$ and R$^3$ are as defined above;

provided that when A is hydrogen at least one of R$^5$, R$^6$ and R$^7$ is —(CR$^1$R$^2$)$_x$R$^3$, and provided that when

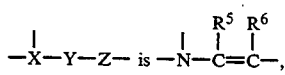

A is —(CR$^1$R$^2$)$_x$R$^3$ and x is 1 to 4 then R$^3$ is —CONHSO$_2$R$^4$; and salts and esters thereof.

The compounds of the invention, with the exception of those in which R$^3$ is —CN, which are intermediates for the production of active compounds, are leukotriene biosynthesis inhibitors and in particular leukotriene antagonists. Thus they are indicated for use in the treatment of diseases in which leukotrienes are a causal mediator.

In the above formula, a C$_{1-4}$ alkyl group includes methyl, ethyl, propyl, isopropyl, butyl and tert. butyl and is preferably methyl or ethyl. An optionally substituted phenyl group is preferably phenyl or phenyl substituted with one or more, preferably one to three, substituents selected from C$_{1-4}$ alkyl, especially methyl, nitro, cyano, carboxyl, amino, hydroxyl, trifluoromethyl, C$_{1-4}$ alkoxy, especially methoxy and ethoxy, and halogen especially fluorine, chlorine or bromine. When substituted, the phenyl group preferably bears a single substituent selected from C$_{1-4}$ alkyl, C$_{1-4}$ alkoxy and halogen, and especially at the ortho position.

When A is —(CR$^1$R$^2$)xR$^3$ or one of the groups R$^5$, R$^6$ and R$^7$ takes this value, R$^1$ and R$^2$ are preferably both hydrogen, and it should be understood that when x is 2, 3 or 4 the repeated units need not be identical. Preferably x is 0 or 1, though in the case of R$^7$ where the group is attached to a ring nitrogen x cannot be 0. Preferred values of —(CR$^1$R$^2$)xR$^3$ are —COOH, tetrazolyl, —CH$_2$COOH and —CH$_2$-tetrazolyl.

A preferred value of

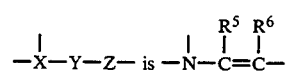

and quinolinyl methoxy group is preferably attached at the meta-position.

A preferred group of compounds of the invention is one of the formula

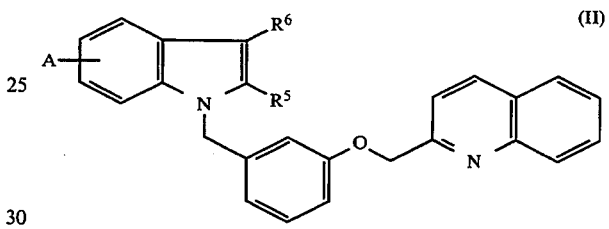
(II)

in which A is hydrogen, —COOH, tetrazolyl or —CONHSO$_2$R$^4$ where R$^4$ is optionally substituted phenyl, R$^5$ and R$^6$ are each hydrogen, C$_{1-4}$ alkyl, —COOH, tetrazolyl, —CH$_2$COOH or —CH$_2$-tetrazolyl, provided that when A is hydrogen, at least one of R$^5$ and R$^6$ is —COOH, tetrazolyl, —CH$_2$COOH, —CH$_2$-tetrazolyl or —CONHSO$_2$R$^4$; and salts and esters thereof.

A further preferred group is one in which A is —CONHSO$_2$R$^4$ and R$^5$ and R$^6$ are each hydrogen, C$_{1-4}$ alkyl, —COOH or tetrazolyl.

It will be appreciated that the compounds of the invention can contain one or more asymmetric carbon atoms which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form.

It is of course, possible to prepare salts of the compounds of the invention and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

It will be appreciated that when $R^3$ —COOH, esters of the compounds of formula (I) are possible. Pharmaceutically-acceptable esters are, of course, preferred and preferred compounds are those in which the group $R^3$ is $C_{1-4}$ alkoxy-carbonyl.

The invention also includes a process for producing a compound of the formula (I) above, which comprises (a) reacting a compound of the formula

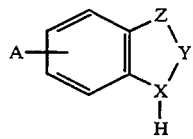
(III)

with a compound of the formula

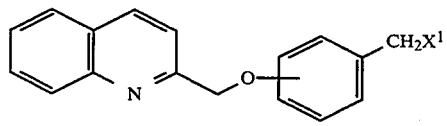
(IV)

where A and

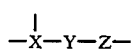

are as defined above, and $R^3$ is —CN or —COOR$^8$ where R$^8$ is an ester group, and $X^1$ is a leaving group;

(b) reacting a compound of the formula

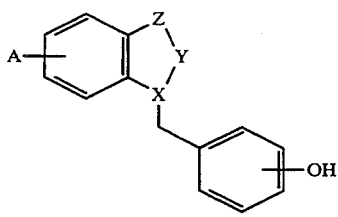
(V)

with a compound of the formula

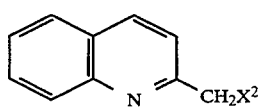

where A and

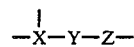

are as defined above, $R^3$ is —CN or —COOR$^8$ where R$^8$ is an ester group, and $X^2$ is halogen; and (c) reacting a compound of the formula

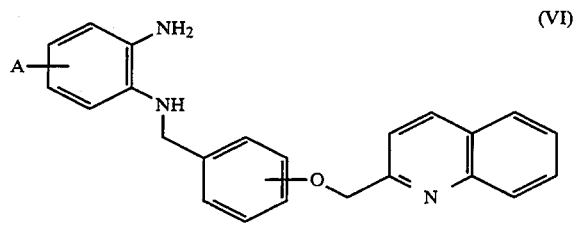
(VI)

where A is as defined above and $R^3$ is —CN or —COOR$^8$ where R$^8$ is an ester group, with a ring cyclising reagent selected from HC(OR$^9$)$_3$ or R$^9$COX$^2$ where $X^2$ is halogen and R$^9$ is $C_{1-4}$ alkyl, or by diazotisation with nitrous acid.

It will be appreciated that the above reactions lead to the preparation of compounds with —CN or —COOR$^8$ groups since these groups protect the reactants against unwanted side reactions and can readily be converted to compounds in which $R^3$ takes other values. For example, intermediates having a nitrile or —COOR$^8$ group can be hydrolysed to the free carboxyl acid-bearing compound. A tetrazolyl derivative can be prepared from the nitrile by reaction with an azide such as for example tributyl tin azide.

When it is desired to prepare a compound in which $R^3$ is —CONHSO$_2$R$^4$, the corresponding compound bearing a —COOR$^8$ group is reacted with the appropriate sulphonamide, R$^4$SO$_2$NH$_2$, or the free carboxylic acid is first combined with an activating group such as dicyclohexyl carbodiimide, 1-(3-dimethylaminopropyl)-3-ethyl carbodiimide, diphenyl carbamoyl chloride and then reacted with sulphonamide, R$^4$SO$_2$NH$_2$. Alternatively the free carboxylic acid can be reacted with the appropriate optionally substituted phenyl sulphonyl isocyanate.

With regard to process variant (a) above, the reaction is preferably carried out at a temperature of from 0° C. to 50° C., for example from 0° C. to 50° C., in an inert organic solvent such as for example dimethylformamide or tetrahydrofuran. The reaction is preferably assisted by the use of an appropriate reagent. For example, when it is intended to form a link with a carbon atom in the heterocylic ring of compound (III) a Grignard reagent such as for example methyl magnesium bromide may be used or if the nitrogen in the heterocyclic ring is substituted silver oxide is preferably employed. When alkylation is required at a nitrogen atom in the heterocyclic ring, a strong base such as for example sodium hydride may be employed.

The reagents of formula (III) are known compounds or can readily be made by well known procedures such as those described by Leimgruber and Batcho, *Organic Synthesis Coll.* Vol. V, 214–224.

Compounds of formula (IV) can be prepared by condensation of the appropriate phenol of formula

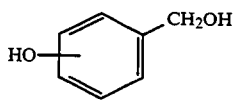

with a quinoline compound of the formula

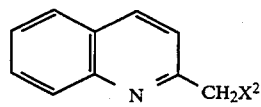

where $X^2$ is halogen. The product is then reacted with appropriate reagents, such as for example N-chlorosuccinimide and triphenylphosphine, to convert the free hydroxyl to a leaving group $X^1$.

With regard to process variant (b), the reaction is preferably carried out at a temperature of from 0° C. to 50° C., for example from 0° C. to 30° c., in an inert organic solvent such as for example tetrahydrofuran or 1,2-dimethoxyethane. The reaction is assisted by the pressure of base and for example suitable bases are sodium hydride or sodium bis(trimethylsilyl) amide.

The intermediate compound (V) is prepared from the compound of formula (VII) by first protecting the phenolic hydroxyl and by reacting the product with a suitable reagent to introduce a leaving group, giving a compound of the formula

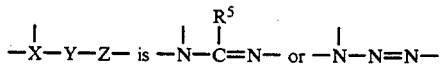   (VII)

where $X^3$ is a protecting group. Reaction with the appropriate heterocycle and removal of the protecting group gives the compound of formula (V).

With regard to process variant (c), it will be appreciated that compounds of formula (I) in which $$-\overset{|}{X}-Y-\overset{|}{Z}- \text{ is } -\overset{|}{N}-\overset{R^5}{\overset{|}{C}}=N- \text{ or } -\overset{|}{N}-N=N-$$

can be prepared by cyclisation to form the imidazolyl or triazolyl rings at a later stage in the synthesis, for example, by a route similar to that of McKee et al. *JACS* 68, 1904 (1946). In the formation of the imidazole ring, in which $$-\overset{|}{X}-Y-\overset{|}{Z}- \text{ is } -\overset{|}{N}-\overset{R^5}{\overset{|}{C}}=N-,$$

the reaction can be carried out at reflux temperature with an appropriate reagent such as triethylformate or an acyl chloride in substantially equimolar proportions. In the formation of a triazole derivative, in which $$-\overset{|}{X}-Y-\overset{|}{Z}- \text{ is } -\overset{|}{N}-N=N-,$$

the cyclisation is effected by diazotisation preferably at a temperature of 0° C. An example of the synthesis of the imidazole derivative is as follows

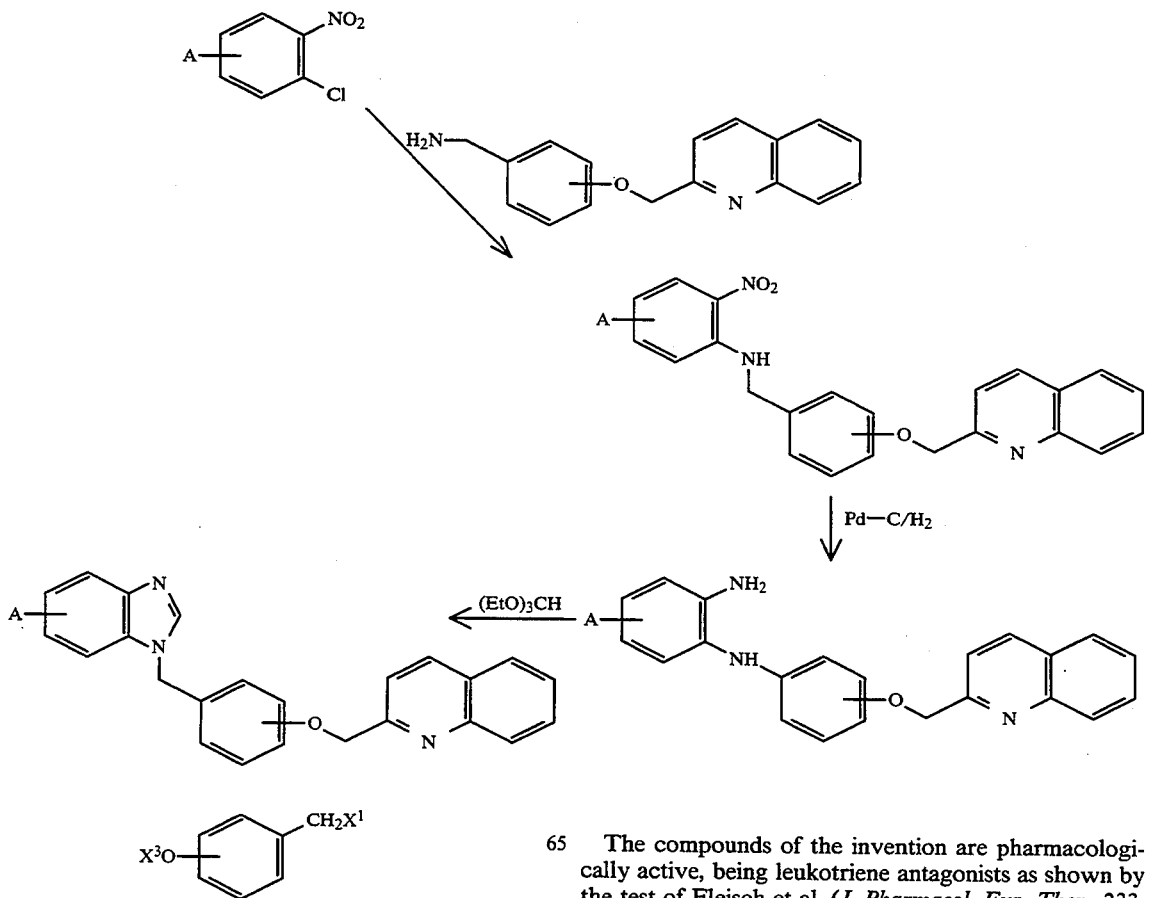

The compounds of the invention are pharmacologically active, being leukotriene antagonists as shown by the test of Fleisch et al. (*J. Pharmacol. Exp. Ther.*, 233, 148–157). Isolated guinea pig tracheal strip was suspended in Krebs solution at 37° C. and aerated with 95% oxygen and 5% carbon dioxide. Concentration response curves to leukotriene ($LTC_4$ and $LTD_4$) were generated and the effects of different concentration of drug investigated. Dissociation constants ($K_B$) of the receptor-inhibitor complex were calculated by the method of Furchgott (Furchgott R. F. *Handbook of Experimented Pharmacology*, New York, Vol. 33 pages 383-385). The compounds are also active in the total pulmonary resistance test (see Fleisch et al. above). Measurement of bronchospasm was recorded as an increase in tracheal resistance produced by $LTD_4$ administered intravenously into anaesthetised artificially ventilated guinea pigs. Also compounds of the invention are active in the in vivo Guinea Pig Pulmonary Function test of Austen and Drazen (1974) *J. Clin. Invest.* 53, 1679-1685 at intravenous dosage levels of from 0.05 µg to 5.0 mg/kg and in a modified "Herxheimer" test (*Journal of Physiology* (London) 117, 251 (1952) at doses of from 25 to 200 mg/kg. The "Herxheimer" test is based on an $LTD_4$-induced bronchospasm in guinea pigs which closely resembles an asthmatic attack in man.

The compounds also inhibit the formation of leukotrienes as indicated by their activity in the test described by Harvey and Osborne, *Journal of Pharmacological Methods*, 9, 147-155 (1983).

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds of the invention also have potential in the treatment of vascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc magnesium stearate and mineral oil. The compositions of the injection may, as is well known in the art, be formulated so as to provide quick, sustained or delayed release of the active ingredient after administration to the patent.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples.

EXAMPLE 1

N-<1-[4-(Quinolin-2-ylmethoxy)benzyl]indol-5-ylcarbonyl>-2-methylbenzenesulphonamide a) 4-(Quinolin-2-ylmethoxy)benzyl chloride i) 4-(Quinolin-2-ylmethoxy)benzyl alcohol A solution of 4-hydroxybenzyl alcohol (14.46 g) in dry dimethylformamide (100 ml) was added dropwise to a stirred suspension of sodium hydride (60% dispersion in oil, 5.6 g), (washed with petroleum spirit 40°-60° C.) in dry dimethylformamide (50 ml) cooled under an atmosphere of nitrogen at 0°-5° C. The mixture was stirred at room temperature for 0.5 hour then re-cooled to 0°-5° C. and a solution of 2-chloromethylquinoline (20.69 g) in dry dimethylformamide (100 ml) added dropwise. The mixture was stirred overnight at room temperature, concentrated in vacuo and diluted with water. The crude product was obtained after cooling and filtration.

ii) 4-(Quinolin-2-ylmethoxy)benzyl chloride

Solid N-chlorosuccinimide (16.69 g) was added in portions to a stirred solution of 4-(quinolin-2-ylmethoxy)benzyl alcohol (26.58 g) and triphenylphosphine (32.89 g) in dichloromethane (600 ml) at 0°-5° C. The mixture was stirred for a further 1.5 hours at 0°-5° C. and then purified rapidly by pouring the mixture onto flash silica and eluting with petroleum spirit 40°-60° C.-diethyl ether (2:1) under vacuum.

b) i) 1-[4-(Quinolin-2-ylmethoxy)benzyl]indole-5-carboxylic acid methyl ester

To a solution of methyl 5-indolecarboxylate (0.54 g) in a mixture of dry dimethylformamide (2 ml) and dry tetrahydrofuran (10 ml) stirred at room temperature, sodium hydride (60% suspended in oil, 0.15 g) was added portionwise. The reaction mixture was stirred for 15 minutes and a solution of 4-(quinolin-2-ylmethoxy)-benzyl chloride (0.88 g) in dry tetrahydrofuran (10 ml) then added dropwise. The reaction mixture was stirred over night at room temperature, evaporated in vacuo and taken up in chloroform. The resulting mixture was washed successively with water and brine, dried over magnesium sulphate, filtered and evaporated in vacuo to dryness. The residue was triturated with boiling methanol and the suspension filtered to give a white solid (0.55 g), m.p. 159°–161° C.

ii) 1-[4-(Quinolin-2-ylmethoxy)benzyl]indole-5-carboxylic acid

A solution of crude methyl ester (Example 1b, part i) (10.1 g) in a mixture of aqueous sodium hydroxide (2M, 30 ml), tetrahydrofuran (80 ml) and methanol (40 ml) was refluxed with stirring overnight. The reaction mixture was cooled, water (200 ml) added, and the turbid solution washed with diethyl ether (3x). The resulting aqueous phase was further diluted with water (200 ml) and acidified with glacial acetic acid (5 ml). The resulting precipitate was filtered, washed with water, cold methanol and diethyl ether and dried in vacuo at 50° C. giving a white solid (6.21 g). A small quantity was crystallised from a mixture of tetrahydrofuran and ethanol.

iii) N-<1-[4-(Quinolin-2-ylmethoxy)benzyl]indol-5-ylcarbonyl>-2-methylbenzene sulphonamide To a stirred suspension of the carboxylic acid (Example 1b, part ii) (3 g), o-toluene sulphonamide (1.38 g) and 4-dimethylaminopyridine (0.45 g) in dichloromethane (40 ml) and water (1 ml), 1-(3-dimethylaminopropyl)-3-ethylcarbodiimide hydrochloride (3.52 g) was added portionwise. The resulting solution was stirred over night. Methanol (2 ml) and 1-(3-dimethylaminopropyl)-3-ethylcarbodiimide hydrochloride (0.5 g) were added and stirring continued for a further 24 hours. The reaction mixture was washed with water (6x), and the organic phase dried over magnesium sulphate, filtered and evaporated. The residue was rapidly chromatographed on flash silica under vacuum using dichloromethane/ethyl acetate (1:9, 3:7, 1:1) and finally ethyl acetate. The partially purified fractions were combined, evaporated in vacuo and subjected to further chromatography on flash silica using petroleum spirit 40°–60° C./diethyl ether (3:2, 1:1, 2:3) as eluent. The pure fractions were combined and evaporated in vacuo to give a white solid (1.7 g), m.p 86°–90° C.

EXAMPLE 2

N-<1-[4-(Quinolin-2-ylmethoxy)benzyl]indol-4-ylcarbonyl>-2-methylbenzenesulphonamide i) 1-[4-(Quinolin-2-ylmethoxy)benzyl]indole-4-carboxylic acid methyl ester This compound was prepared from methyl 4-indole carboxylate and 4-(quinolin-2-ylmethoxy)benzyl chloride (Example 1a by the method described in Example 1b part i), m.p. 128°–131° C.

ii) 1-[4-(Quinolin-2-ylmethoxy)benzyl]indole-4-carboxylic acid

This compound was prepared from the methyl ester (Example 2, part i) by the method described in Example 1b, part ii., m.p. 181°–187° C.

iii) N-<1-[4-(Quinolin-2-ylmethoxy)benzyl]indol-4-ylcarbonyl>-2-methylbenzenesulphonamide This compound was prepared from the carboxylic acid (Example 2, part ii) by the method described in Example 1b, part iii. The product was crystallised from isopropyl alcohol, m.p. 85°–88° C.

EXAMPLE 3

N-<1-[4-(Quinolin-2-ylmethoxy)benzyl]indole-6-ylcarbonyl>-2-methylbenzenesulphonamide i) 1-[4-(Quinolin-2-ylmethoxy)benzyl]indole-6-carboxylic acid methyl ester This compound was prepared from methyl 6-indole carboxylate and 4-quinolin-2-ylmethoxy)benzyl chloride (Example 1a) by the method described in Example 1b, part i, m.p. 125°–126° C.

ii) 1-[4-(Quinolin-2-ylmethoxy)benzyl]indole-6-carboxylic acid

This compound was prepared from the methyl ester (Example 3, part i) by the method described in Example 1b, part ii, m.p. 221°–224° C.

iii) N-<1-[4-(Quinolin-2-ylmethoxy)benzyl]indol-6-ylcarbonyl>-2-methylbenzenesulphonamide.

This compound was prepared from the carboxylic acid (Example 3, part ii) by the method described in Example 1b, part iii. A sample was crystallised from ethanolic hydrogen chloride as its hydrochloride salt, m.p. 190°–195° C.

EXAMPLE 4

N-<1-[4-(Quinolin-2-ylmethoxy)benzyl]indol-7-ylcarbonyl>-2-methylbenzenesulphonamide i) 1-[4-(Quinolin-2-ylmethoxy)benzyl]indole-7-carboxylic acid methyl ester This compound was prepared from methyl 7-indole carboxylate and 4-(quinolin-2-ylmethoxy)benzyl chloride (Example 1a) by the method described in Example 1b, part i. The residue was purified by chromatography on flash silica using petroleum spirit 40°–60° C./diethyl ether (2:1, 7:5) as eluent.

ii) 1-[4-(Quinolin-2-ylmethoxy)benzyl]indole-7-carboxylic acid

This compound was prepared from the methyl ester (Example 4, part i) by the method described in Example 1b, part ii, m.p. 210°–214° C.

iii) N-<1-[4-(Quinolin-2-ylmethoxy)benzyl]indol-7-ylcarbonyl>-2-methylbenzenesulphonamide This compound was prepared from the carboxylic acid (Example 4, part ii) by the method described in Example 1b, part iii, m.p. 173°–176° C.

EXAMPLE 5

N-<1-[3-(Quinolin-2-ylmethoxy)benzyl]indol-6-ylcarbonyl<-2-methylbenzenesulphonamide a) 3-(Quinolin-2-ylmethoxy)benzyl chloride i) 3-(Quinolin-2-ylmethoxy)benzyl alcohol This compound was prepared from 3-hydroxybenzyl alcohol and 2-chloromethylquinoline by the method described in Example 1a, part i.

ii) 3-(Quinolin-2-ylmethoxy)benzyl chloride

This compound was prepared from 3-(quinolin-2-ylmethoxy)benzyl alcohol (Example 5a, part i) by the method described in Example 1a, part ii.

b) i) 1-[3-(Quinolin-2-ylmethoxy)benzyl]indole-6-carboxylic acid methyl ester

This compound was prepared from methyl 6-indole carboxylate and 3-(quinolin-2-ylmethoxy)benzyl chloride (Example 5a) by the method described in Example 1b, part i.

ii) 1-[3-(Quinolin-2-ylmethoxy)benzyl]indole-6-carboxylic acid

This compound was prepared from the methyl ester (Example 5b, part i) by the method described in Example 2b, part ii. The product was crystallised from tetrahydrofuran, m.p. 193°–196° C.

iii) N-<1-[3-(Quinolin-2-ylmethoxy)benzyl]indol-6-ylcarbonyl<-2-methylbenzanesulphonamide This compound was prepared from the carboxylic acid (Example 5b, part ii) by the method described in Example 1b, part iii, m.p. 187°–190° C.

EXAMPLE 6

N-<1-[3-(Quinolin-2-ylmethoxy)benzyl]indole-5-ylcarbonyl>-2-methylbenzenesulphonamide i) 1-[3-(Quinolin-2-ylmethoxy)benzyl]indole-5-carboxylic acid methyl ester This compound was prepared from methyl-5-indole carboxylate and 3-(quinolin-2-ylmethoxy)benzyl chloride (Example 5a) by the method described in Example 1b, part i.

ii) 1-[3-(Quinolin-2-ylmethoxy)benzyl]indole-5-carboxylic acid

This compound was prepared from the methyl ester (Example 6, part i) by the method described in Example 1b, part ii.

iii) N-<1-[3-(Quinolin-2-ylmethoxy)benzyl]indol-5-ylcarbonyl>-2-methylbenzenesulphonamide This compound was prepared from the carboxylic acid (Example 6, part ii) by the method described in Example 1b, part iii.

EXAMPLE 7

N-<1-[4-(Quinolin-2-ylmethoxy)benzyl]indol-5-ylcarbonyl>-2-nitrobenzenesulphonamide This compound was prepared from the carboxylic acid (Example 1b, part ii) and 2-nitrobenzenesulphonamide by the method described in Example 1b, part iii. The product was crystallised from isopropyl alcohol, m.p. 95°–99° C.

EXAMPLE 8

N-<1-[4-(Quinolin-2-ylmethoxy)benzyl]indol-5-ylcarbonyl>-4-methoxybenzenesulphonamide This compound was prepared from the carboxylic acid (Example 1b, part ii) and 4-methoxybenzenesulphonamide by the method described in example 1b, part iii. The product was crystallised from isopropyl alcohol, m.p. 179°–181° C.

EXAMPLE 9

N-<1-[4-(Quinolin-2-ylmethoxy)benzyl]indol-5-ylcarbonyl>-4-chlorobenzene sulphonamide This compound was prepared from the carboxylic acid (Example 1b, part ii) and 4-chlorobenzenesulphonamide by the method described in Example 1b, part iii. The product was crystallised from isopropyl alcohol, m.p. 96°–100° C.

EXAMPLE 10 i) 1-methylindole-6-carboxylic acid methyl ester

To a stirred solution of methyl 6-indolecarboxylate (5 g) in dry dimethylformamide (30 ml) cooled to 5° C., sodium hydride (60% dispersion in oil, 1.49 g) was added portionwise. The reaction mixture was stirred at 5° C. for 0.5 hour, then a solution of methyliodide (12.18 g) in dry dimethylformamide (10 ml) was added dropwise. After 2 hours, the reaction mixture was diluted with water and the product obtained, after cooling and filtration.

ii) 1-Methyl-3-[4-(quinolin-2-ylmethoxy)benzyl]indole-6-carboxylic acid methyl ester To a stirred solution of 1-methylindole-6-carboxylic acid methyl ester (Example 10, part i) (1.5 g) and 4-(quinolin-2-ylmethoxy)benzyl chloride (2.43 g) in dioxan (15 ml), silver oxide (2 g) was added and the suspension heated at 70° C. overnight. The solvent was removed in vacuo, the residue ultrasonicated with ethylacetate and insoluble material removed by filtration through celite. The filtrate was evaporated to dryness and the residue purified by chromatography on flash silica, eluting with petroleum spirit 40°–60° C./diethyl ether (1:1) to give the product as a white solid. A small quantity was crystallised from petroleum spirit 40°–60° C./diethyl ether (1:1).

iii) 1-Methyl-3-[4-(quinolin-2-ylmethoxy)benzyl]indole-6-carboxylic acid

A solution of the methyl ester (Example 10, part ii) (1.73 g) in aqueous sodium hydroxide (2M, 5.9 ml), tetrahydrofuran (20 ml) and methanol (10 ml) was refluxed with stirring overnight. The reaction mixture was cooled, diluted with water until turbid and washed with diethyl ether (2×). The aqueous phase was acidified with acetic acid and the resulting precipitate filtered, washed with water and dried in vacuo at 50° C. to give the product as a white solid (1 g). A small amount was crystallised from tetrahydrofuran/ethanol m.p. 208°–212° C.

iv) N-<1-Methyl-3-[4-(quinolin-2-ylmethoxy)benzyl]-indol-6-ylcarbonyl>-2-methylbenzenesulphonamide To a stirred suspension of the carboxylic acid (Example 10, part iii) (205 mg), o-toluenesulphonamide (91 mg) and 4-dimethylaminopyridine (30 mg) in dichloromethane (10 ml) and water (2 drops), 1-(3-dimethylaminopropyl)-3-ethylcarbodiimide hydrochloride (0.28 g) was added portionwise. The resulting solution was stirred over night, methanol (0.5 ml) and 1-(3-dimethylaminopropyl)-3-ethylcarbodiimide hydrochloride (0.2 g) were added and stirring continued for a further 24 hours. The solvents were removed in vacuo and the residue purified by chromatography on flash silica using diethyl ether and then 1,4-dioxan, as eluent, to give a white solid, m.p. 92°–95° C.

EXAMPLE 11

1-Propyl-3-[4-(quinolin-2-ylmethoxy)benzyl]indole-6-carboxylic acid i) 1-Propylindole-6-carboxylic acid methyl ester This compound was prepared from methyl-6-indolecarboxylate and propyliodide by the method described in Example 10, part i. The reaction mixture was worked up by removal of the dimethylformamide in vacuo and the residue partitioned between diethyl ether and water. The organic phase was further washed with water and brine, dried and evaporated. The resulting oil was purified by chromatography on flash silica eluting with petroleum spirit 40°–60° C.-diethyl ether (9:1) to give the product as a colourless oil.

ii) 1-Propyl-3-[4-(quinolin-2-ylmethoxy)benzyl]indole-6-carboxylic acid methyl ester This compound was prepared from the methyl ester (Example 22, part i) and 4-(quinoline-2-ylmethoxy)benzyl chloride (Example 1a) by the method described in Example 10, part ii.

iii) 1-Propyl-3-[4-(quinolin-2-ylmethoxy)benzyl]indole-6-carboxylic acid

This compound was prepared from the methyl ester (Example 11, part ii) by the method described in Example 10, part iii, m.p. 80°-82° C.

EXAMPLE 12

3-[4-(Quinolin-2-ylmethoxy)benzyl]indole-4-carboxylic acid i) 3-[4-(Quinolin-2-ylmethoxy)benzyl]indole-4-carboxylic acid methyl ester A solution of methyl magnesium bromide in n-butyl ether (1.0M, 10.3 ml) was added dropwise to a solution of methyl indole-4-carboxylate (1.5 g) in dry dimethylformamide (15 ml) stirred under an atmosphere of nitrogen at room temperature. The mixture was stirred at room temperature for 20 minutes then a solution of 4-(quinolin-2-ylmethoxy)benzyl chloride (Example 1a) (2.35 g) in dry dimethylformamide (10 ml) added dropwise. The mixture was stirred at room temperature overnight, concentrated in vacuo, diluted with ethyl acetate and washed with water and a saturated solution of ammonium chloride; the organic phase was dried, filtered and evaporated. The residue was purified by chromatography on flash silica, eluting with petroleum spirit 40°-60° C.—diethyl ether (1:1) to give the product as a white solid. A small quantity was crystallised from petroleum spirit 40°-60° C.—diethyl ether (1:1), m.p. 148°-150° C.

ii) 3-[4-(Quinolin-2-ylmethoxy)benzyl]indole-4-carboxylic acid

This compound was prepared from the methyl ester (example 12, part i) by the method described in Example 10, part iii, m.p. 209°-211° C.

EXAMPLE 13

3-[4-(Quinolin-2-ylmethoxy)benzyl]indole-5-carboxylic acid i) 3-[4-(Quinolin-2-ylmethoxy)benzyl]indole-5-carboxylic acid, methyl ester This compound was prepared from methyl indole-5-carboxylate and 4-(quinolin-2-ylmethoxy)benzyl chloride (Example 1a) by the method described in Example 12, part i, m.p. 179°-180° C.

ii) 3-[4-(Quinolin-2-ylmethoxy)benzyl]indole-5-carboxylic acid

This compound was prepared from the methyl ester (Example 13, part i) by the method described in Example 10, part iii, m.p. 227°-228° C.

EXAMPLE 14

3-[4(Quinolin-2methoxy)benzyl]indole-6-carboxylic acid i) 3-[4-(Quinolin-2ylmethoxy)benzyl]indole-6-carboxylic acid, methyl ester This compound was prepared from methyl indole-6-carboxylate and 4-(quinolin-2-ylmethoxy)benxyl chloride (Example 1a) by the method described in Example 12, part i.

ii) 3-]4-(Quinolin-2-ylmethoxy)benxyl]indole-6-carboxylic acid

This compound was prepared from the methyl ester (Example 14, part i) by the method described in Example 10, part iii, m.p. 230°-235° C.

EXAMPLE 15

3-[3-(Quinolin-2-ylmethoxy)benzyl]indole-6-carboxylic acid i) 3-[3-(Quinolin-2-ylmethoxy)benzyl]indole-6-carboxylic acid methyl ester This compound was prepared from methyl indole-6-carboxylate and 3-(quinolin-2-ylmethoxy)benzyl chloride (Example 5a) by the method described in Example 10, part ii.

ii) 3-[3-(Quinolin-2-ylmethoxy)benzyl]indole-6-carboxylic acid

This compound was prepared from the methyl ester (Example 15, part i) by the method described in Example 10, part iii, m.p. 221°-225° C.

EXAMPLE 16

3-[4-(Quinolin-2-ylmethoxy)benzyl]indole-1-acetic acid i) Indole-1-acetic acid methyl ester This compound was prepared from indole and methyl bromoacetate by the method described in Example 10, part i. The reaction mixture was worked up by concentrating in vacuo, diluting with water and extracting with ethyl acetate (3x). The combined extracts were washed with water (3x) and brine, dried and evaporated to an oil. The residue was purified by chromatography on flash silica eluting with petroleum spirit 40°-60° C.—diethyl ether (5:1, 2:1) to give the product.

ii) 3-[4-)Quinolin-2-ylmethoxy)benzyl]indole-1-acetic acid methyl ester

This compound was prepared from the methyl ester (Example 16, part i) and 4-(quinolin-2-ylmethoxy)benzyl chloride (Example 1a) by the method described in Example 10, part ii. The residue was purified by chromatography on flash silica, eluting with dichloromethane-petroleum spirit 40°-60° C. (3:1, 4:1) and dichloromethane. The product was crystallised from diethyl ether.

iii) 3-]4-(Quinolin-2-ylmethoxy)benzyl]indole- 1-acetic acid

This compound was prepared from the methyl ester (Example 16, part ii) by the method described in Example 16, part ii, m.p. 189°-192° C.

EXAMPLE 17

1-[4-(Quinolin-2-ylmethoxy)benzyl]indol-3-acetic acid i) 1-[4-(Quinolin-2-ylmethoxy)benzyl]indol-3-acetic acid methyl ester This compound was prepared from indole-3-acetic acid methyl ester (J.C.S., 2581, 1955) and 4-(quinolin-2-ylmethoxy)benzyl chloride (example 1a) by the method described in Example 1b, part i.

ii) 1-[4-)Quinolin-2-ylmethoxy)benzyl]indol-3-acetic acid

This compound was prepared from the methyl ester (Example 17, part i) by the method described in Example 16, part iii. The product was recrystallised from ethyl acetate, m.p. 163°-166° C.

EXAMPLE 18

5-<3-[4-(Quinolin-2-ylmethoxy)benzyl]indol-6-yl>-1H-tetrazole i) 6-cyano-3-[4-(quinolin-2-ylmethoxy)benzyl]indole This compound was prepared from 6-cyanoindole and 4-(quinolin-2-ylmethoxy)benzyl chloride (Example 1a) by the method described in Example 12, part i). ii) 5-<3-[4-(Quinolin-2-ylmethoxy)benzyl]-6-yl>-1H-tetrazole A solution of the nitrile (Example 18, part i) (0.55 g) and tributyltin azide (0.52 g) in 1,2-dimethoxyethane (15 ml) was heated with stirring for 24 hours, during which the solvent was allowed to evaporate. The residue was heated with aqueous hydrochloric acid (2M) and methanol and the solvents then removed in vacuo. The residue was chromatographed on flash silica using ethyl acetate as eluent. The product was crystallised from ethyl acetate-petroleum spirit 40°-60° C., m.p. 212°-218° C.

EXAMPLE 19

5-<1-[3-(Quinolin-2-ylmethoxy)benzyl]indol-5-yl>-1H-tetrazole i) 5-Cyano-1-[3-(quinolin-2-ylmethoxy)benzyl]indole This compound was prepared from 5-cyanoindole and 3-(quinolin-2-ylmethoxy)benzyl chloride (Example 5a) by the method described in Example 16, part ii. The residue was crystallised from ethanol.

ii) 5-<1-[3-(Quinolin-2-ylmethoxy)benzyl]indol-5-yl>-1H-tetrazole

This compound was prepared from the nitrile (Example 19, part i) by the method described in Example 18, part ii. The residue was chromatographed on flash silica using dichloromethane and dichloromethane-methanol (9:5) as eluent. The product crystallised from ethanol, m.p. 222°-225° C.

EXAMPLE 20

Soft gelatine capsule

Each soft gelatine capsule contains:

| Active ingredient | 150 mg |
|---|---|
| Arachis oil | 150 mg |

After mixing together, the blend is filled into soft gelatine capsules using the appropriate equipment.

EXAMPLE 21

Hard gelatine capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 22

Aerosol

| Active ingredient | 10 mg |
|---|---|
| Ethanol | 50 mg |

| Dichlorodifluoromethane (Propellant 12) | 658 mg |
|---|---|
| Dichlorotetrafluoroethane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 to 100 μl equivalent to 0.5-1 mg active ingredient.

We claim:

1. A compound of the formula:

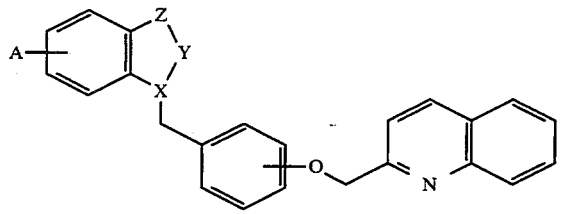

and salts and esters thereof in which

A is hydrogen or —(CR$^1$R$^2$)$_x$R$^3$, R$^1$ and R$^2$ are each hydrogen or C$_{1-4}$ alkyl and R$^3$ is —COOH, tetrazolyl, or —CONHSO$_2$R$^4$ where R$^4$ is phenyl or phenyl substituted with one to three substituents selected from C$_{1-4}$ alkyl, nitro, cyano, carboxyl, amino, hydroxyl, trifluoromethyl, C$_{1-4}$ alkoxy, and halogen; and

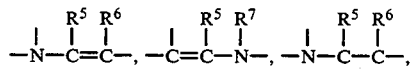 is selected from

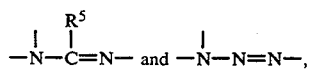

where R$^5$ and R$^6$ are each hydrogen, C$_{1-4}$ alkyl or —(CR$^1$R$^2$)$_x$R$^3$ where X, R$^1$, R$^2$, and R$^3$ are as defined above, and R$^7$ is hydrogen, C$_{1-4}$ alkyl or —(CR$^1$R$^2$)$_x$R$^3$, and R$^1$, R$^2$ and R$^3$ are as defined above;

provided that when A is hydrogen at least one of R$^5$, R$^6$, and R$^7$ is —(CR$^1$R$^2$)$_x$R$^3$, and provided that when

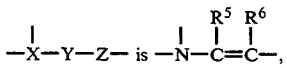

A is —(CR$^1$R$^2$)$_x$R$^3$ and R3 is —CONHSO$_2$R$^4$; and further provided that x is 0 or 1 to 4 unless;

 (i)

then x cannot be 0; or

 (ii):

then x cannot be 0.

2. A compound according to claim 1, in which

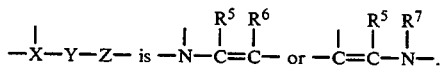

3. A compound according to claim 2, in which A is —COOH, tetrazolyl, —CH₂COOH or —CH₂-tetrazolyl.

4. A compound of the formula:

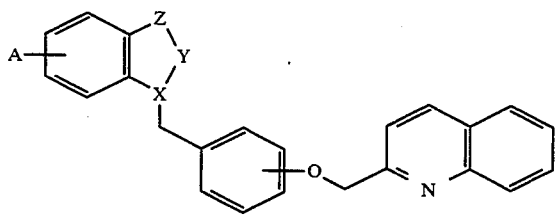

and salts and esters thereof in which A is hydrogen, —COOH, tetrazolyl or —CONHSO$_2$R$^4$ where R$^4$ is phenyl or phenyl substituted with one to three substituents selected from C$_{1-4}$ alkyl, nitro, cyano, carboxyl, amino, hydroxyl, trifluoromethyl, C$_{1-4}$ alkoxy, and halogen, R$^5$ and R$^6$ are each hydrogen, C$_{1-4}$ alkyl, —COOH, tetrazolyl, —CH$_2$COOH, —CH$_2$-tetrazolyl, provided that when A is hydrogen, at least one of R$^5$ and R$^6$ is —COOH, tetrazolyl, —CH$_2$COOH, —CH$_2$-tetrazolyl or —CONHSO$_2$R$^4$.

5. A pharmaceutical formulation comprising a compound according to claim 1, or a pharmaceutically-acceptable salt or ester thereof, together with a pharmaceutically-acceptable carrier or diluent therefor.

6. A method of treating an animal, including a human, suffering from bronchospasms and asthma; which method comprises administering an effective amount of a compound according to claim 1, or a pharmaceutically acceptable salt or ester thereof.

7. A method of treating an animal suffering from or susceptible to a disease in which leukotrienes are a causal mediator, which comprises administering an effective amount of a compound according to claim 1, or a pharmaceutically-acceptable salt or ester thereof.

* * * * *